United States Patent [19]

Williamson et al.

[11] Patent Number: 5,368,552
[45] Date of Patent: Nov. 29, 1994

[54] ORTHOTIC HIP BRACE

[75] Inventors: Craig D. Williamson; Frederic C. Feiler, both of Colorado Springs, Colo.

[73] Assignee: Rocky Mountain Prosthetics Orthotics, Colorado Springs, Colo.

[21] Appl. No.: 90,879

[22] Filed: Jul. 13, 1993

[51] Int. Cl.⁵ .............................................. A61F 5/00
[52] U.S. Cl. ...................................... 602/23; 602/16; 623/17
[58] Field of Search .................... 602/23, 24, 16, 5; 623/27, 22, 48

[56] References Cited

U.S. PATENT DOCUMENTS 4,881,532  11/1989  Borig et al. ........................... 602/16
4,905,678  3/1990  Cumins et al. ....................... 602/16

Primary Examiner—Richard J. Apley
Assistant Examiner—Beverly A. Meindl
Attorney, Agent, or Firm—Beaton & Swanson

[57] ABSTRACT

A joint for a hip brace or prosthetic which allows adjustable degrees of pivoting of the leg, rotation of the leg and abduction/adduction of the leg.

9 Claims, 3 Drawing Sheets

ORTHOTIC HIP BRACE

BACKGROUND OF THE INVENTION

Many individuals require partial immobilization, to protect a traumatized joint. Ideally, this partial immobilization would allow the joint to move through a predetermined range of motion that is necessary for limited locomotion and healing, but not through a range of motion that is injurious to the joint or painful to the individual. Further, it would also be ideal to be able to increase mobility in a controlled manner as the joint begins to heal.

Referring to FIG. 1 it can be seen that the hip joint is a ball-and-socket joint formed by the joining of the head of the femur 60 into the cup-shaped cavity of the pelvic bone, referred to as the acetabulum 62. Being a ball-and-socket joint the movements of the hip are extensive, consisting of three axes of rotation—flexion-extension (the bending motion of the hip joint), internal and external rotation (rotation of the lower limb about its longitudinal axis) and abduction-adduction (the lateral motion of the hip joint). The normal active ranges of motion for the hip joint are approximately: hip flexion 121°, hip extension 19°, hip abduction 43°, hip internal rotation 45°, and hip external rotation 45°. Roach, K. E. and Miles, T. P., "Normal Hip and Knee Active Range of Motion: The Relationship to Age", *Physical Therapy*, 1991, 71:9, 656–665.

Because the neck of the femur 64 is a long segment of bone which joins the shaft 66 at an abrupt angle all movements of the thigh result from movements of the head and neck segment rather than the shaft of the femur. As an example, flexion and extension of the thigh are caused by rotation of the head and neck segment of the femur along an axis as shown in FIG. 1. Furthermore, the head and neck segment rotate outward as the leg flexes forward. During abduction and adduction of the thigh, the head and neck segment move within the plane established by their angle, and result from a bending in the joint with some rotation caused by the normally forward inclination of the neck of the femur. In other words, rather than merely bending about a pivot axis, the normal motion of the hip joint includes pivoting at an axis that slides in relation to the joint to produce a "component motion" in more than one plane.

Numerous devices have been developed for immobilizing the hip joint. Illustrative of traditional prior art devices is U.S. Pat. No. 4,481,941 by Rolfes, which accommodates the flexion-extension or bending motion of the leg while preventing any lateral or rotational movement. Thus, a major drawback of traditional devices is that they do not mimic the ball-and-socket movement of hip joint in that they pivot at a single fixed axis and move through a single plane. Typical of more recent prior art devices is U.S. Pat. No. 4,881,532 by Borig, et al. The more recent devices are designed to provide for two axes of motion—flexion-extension and abduction-adduction. The Borig device, for example, is comprised of an upper and lower control arm which contains two hinges. One hinge provides for a range of rotation of the hip brace during flexion and extension of the hip and the second hinge provides for a range of rotation of the brace during abduction and adduction of the hip. The Borig device can be adjusted for free abduction motion up to 30°.

It is readily apparent that none of the prior art devices make any attempt to account for the rotation of the lower limb about its longitudinal axis as the leg flexes forward or laterally. Accordingly, there is a need for an orthopedic hinge for use with hip joint braces that provides for free external and internal rotation of the hip joint within a controlled range.

SUMMARY OF THE INVENTION

The present invention is a device for use as a hinge in an orthotic brace, such as a hip brace. The device is configured to accommodate the bending of the hip joint about a moving axis during flexion and extension of the hip. It is also configured to allow the hip joint to twist—that is to rotate about its longitudinal axis. Finally, the device is configured to allow for a very limited range of lateral motion of the hip joint.

The invention includes a first housing unit containing a rotation means which accommodates the twisting or rotation of the femur about its longitudinal axis and also accommodates a limited amount of lateral movement of the femur. The invention also includes a second housing unit containing a pivot means which accommodates the bending motion of the hip joint during flexion-extension. Finally, the invention includes a connection means for attachment of the rotation means to the pivot means.

The connection means between the rotation means and the pivot means includes a top head portion which projects into the first housing unit and a lower cylindrical portion which projects into the second housing unit. The upper and lower portions of the connection means are attached to one another by a cylindrical shaft which is located within the first housing unit.

The first housing unit contains a top and a bottom side which when assembled form a sleeve around the shaft and the head of the connecting means. The shaft and head of the connection means are allowed to freely rotate in the sleeve formed by the first housing unit thus, forming a rotation means. This rotation provides a first range of motion that accommodates the twisting or rotation of the femur about its longitudinal axis. The cylinder which forms the lower portion of the connection means is positioned on an axle within the second housing unit. The cylinder freely rotates about this axle thereby forming the pivot means that imparts a second range of motion which accommodates the bending motion of the hip during flexion-extension.

The invention can be used as a hinge in a brace or a prosthetic which functions to limit movement in the hip joint. As an orthotic hip hinge, the invention serves to protect the injured or weakened joint against further injury or weakening by requiring the joint to bend only in the predetermined manner corresponding to the natural uninjured bending of the joint. The hinge of this invention better approximates the ball-and-socket motion of the hip joint and can be easily adjusted to provide greater mobility as the joint heals.

BRIEF DESCRIPTION OF THE DRAWINGS

FIG. 4A is an elevational view showing one side of the first housing unit. FIG. 4B is an elevational view showing the other side of the first housing unit. FIG. 4C is a top view of the fully assembled first housing unit.

DETAILED DESCRIPTION OF THE INVENTION

The orthotic hinge of this invention is designed for use with a brace for supporting the hip joint. The device includes two housings configured such that they allow for both pivoting and rotation plus abduction-adduction. Furthermore, the two housings are designed to operate in conjunction with each other to closely mimic the ball-and-socket movement of the hip joint. This invention will be described first with a discussion of the first housing which accommodates the twisting or rotational motion of the hip joint about its longitudinal axis and within a very limited range the abduction-adduction (or the lateral motion) of the hip joint and then with a discussion of the second housing which accommodates the flexion-extension or the bending motion of the hip joint.

Figure 1:
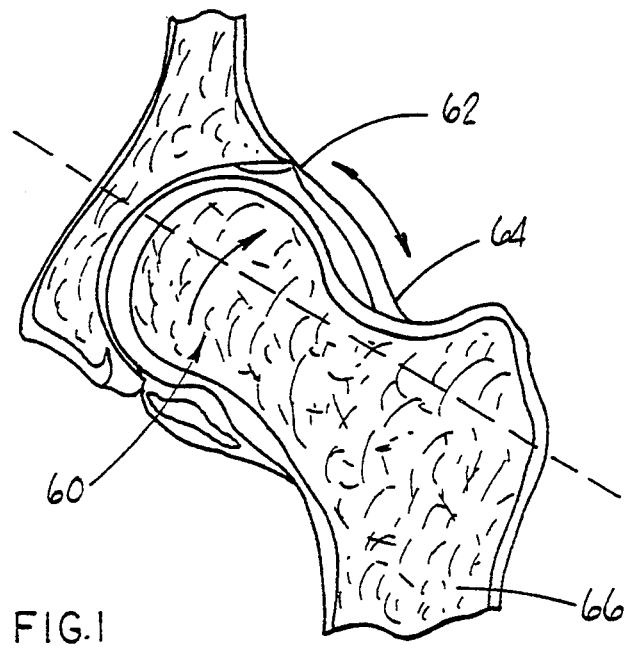
FIG. 1 shows a sectional view of the pelvic bone and the upper femur where they meet at a hip joint.
Figures 2, 3:
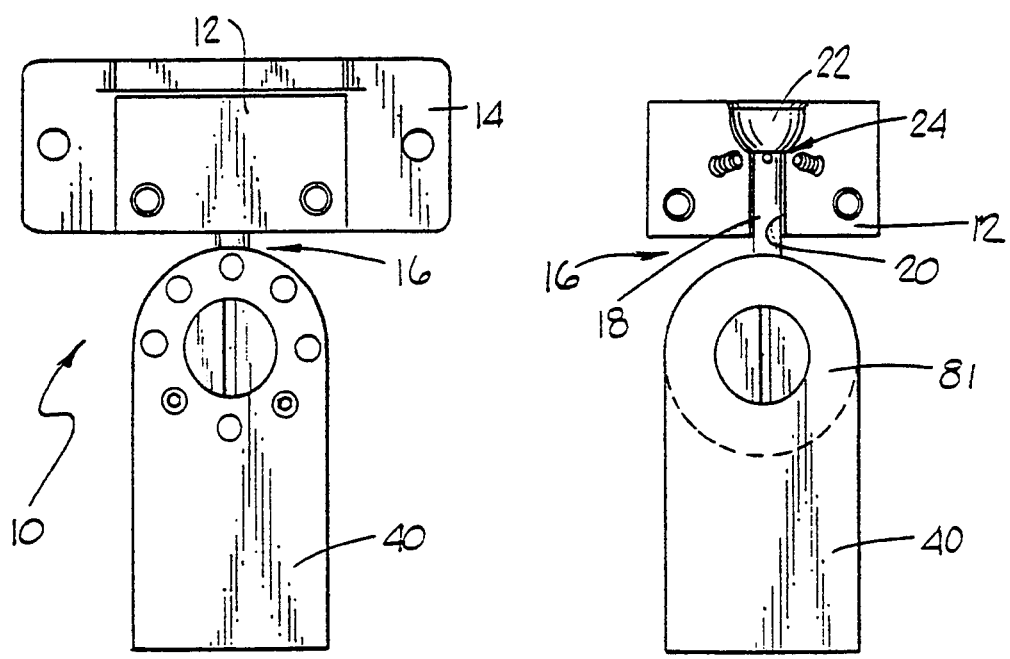
FIG. 2 is an elevational view of the present invention.
FIG. 3 is front elevational view of this invention with one side of the housing unit removed showing the position of the connection means within the first and second housing units.
Figure 9:
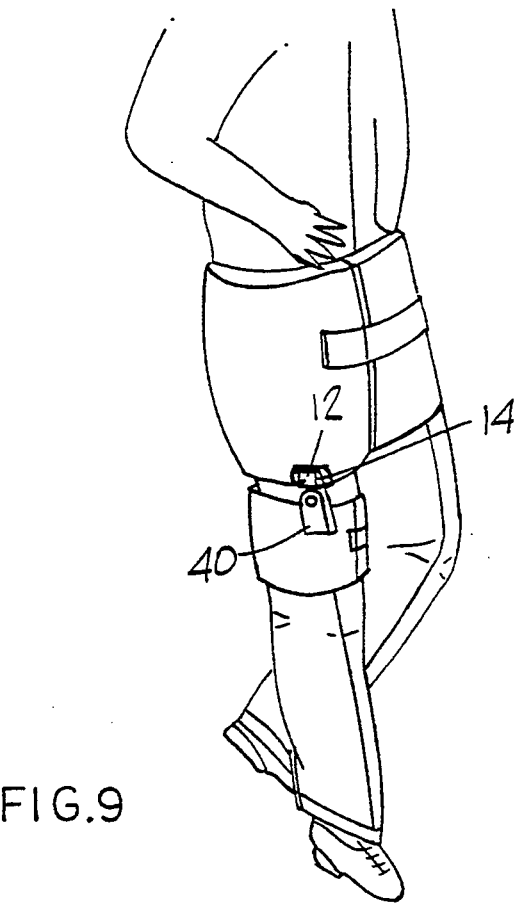
FIG. 9 is a view of the fully assembled invention showing the multiple axes of rotation.

Referring to FIG. 2 it can be seen that the invention 10 includes a first housing unit 12 which is attached, by means of bracket 14, to that portion of a hip brace that fits around the waist and a second housing unit 40 which is attached to the portion of the hip brace that is attached to the upper leg (see FIG. 9). The first and second housing units are connected to each other by means of a connection mechanism 16.

The first housing unit contains a rotation means which provides for a controlled range of external and internal rotation during the twisting of the hip joint. The design of this rotation means also provides for a very limited range of motion during abduction-adduction or lateral movement of the hip joint. The second housing unit contains a pivot means which provides for a controlled range of motion during flexion and extension of the hip joint. As will be discussed in more detail below the two housings receive connection mechanism 16 and thus by design necessarily operate in concert to better approximate the ball-and-socket motion of the hip joint.

The first housing unit and the connection means contained therein are shown in more detail in FIGS. 3 and 4A-4C. As can be seen in FIG. 3 the connection means 16 is comprised of a shaft 18 having a head 22 at one end and a wheel 81 at the opposite end. The head 22 and shaft 18 of the connection means are contained within the first housing unit 12 and make up the rotation means. The wheel 81 is contained within the second housing unit 40 and makes up the pivot means. The shaft 18 projects outwardly from the second housing unit and enters the first housing unit through a circular opening 20 at the bottom of the first housing unit. A pin 24 projects radially outward from one side of the shaft 18.

Figures 4A, 4B:
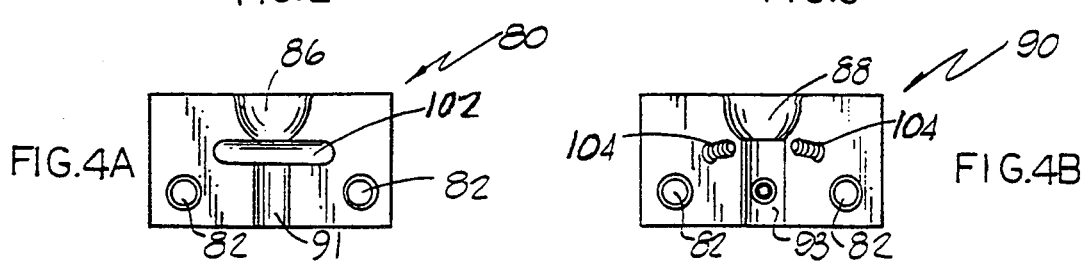
FIGS. 4A–4C are a series of views of the first housing unit.
Figure 4C:
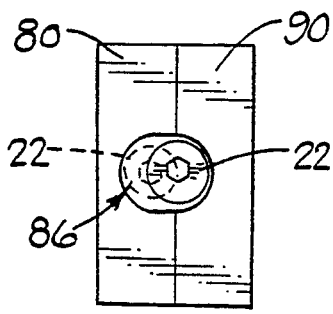

As can be seen in FIGS. 4A and 4C the first housing unit 12 contains a side 80 and a side 90 which are secured by screws through screw holes 82. Each side of the first housing unit contains a groove 91 and 93 equal in length and having a depth of slightly more than one-half of the diameter of the shaft 18 of the connection means 16. When assembled and secured the two sides of the housing unit, therefore, form a sleeve around the shaft 18 of the connection means. At the top of each side of the first housing unit there is a slightly larger groove 86 and 88, respectively, which when the unit is assembled form a sleeve around the head 22 of the connection means. Referring to FIG. 4C it can be seen that on the top side of the housing unit 80 this groove 86 is slightly larger than the head 22 of the connecting means. This allows for very limited lateral movement of the head 22 as shown by the dotted lines in FIG. 4C. In operation, this movement accommodates light abduction and adduction movement of the braced hip joint.

With further reference to FIGS. 4A and 4B one side 80 of the housing unit contains a partly circumferential slot 102 and the other side 90 contains stoppers 104 in the form of two set screws. When assembled the pin 24 extending from the shaft 18 is positioned in the slot 102 and the shaft is allowed to freely rotate in the sleeve formed until the pin meets the stops 104. The stops are adjustable by screwing and unscrewing the set to permit free rotation up to a maximum of 45 degrees in each direction. This rotation accommodates the twisting or the rotation of the femur about its longitudinal axis.

Figure 5:
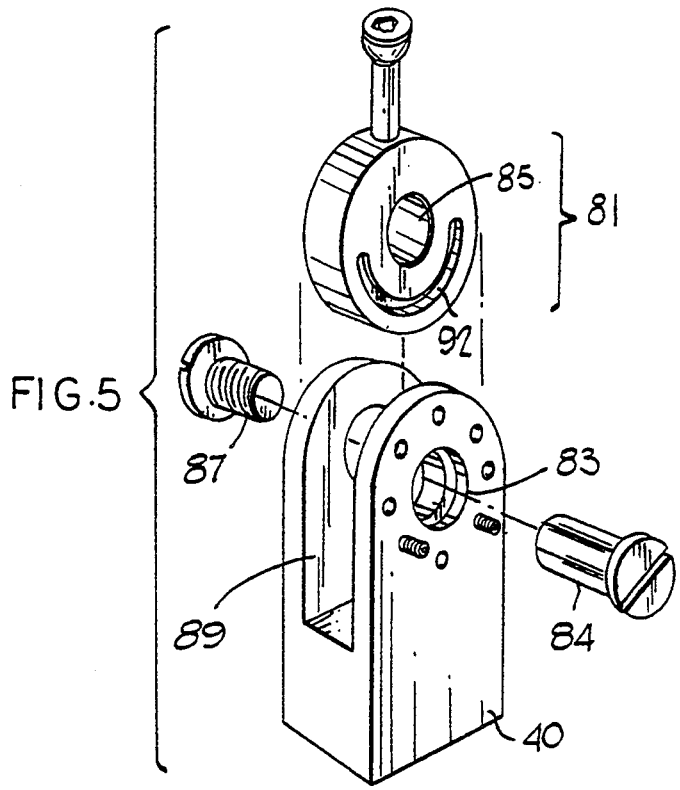
FIG. 5 is an exploded perspective view of the second housing unit and connection means of this invention.

A perspective view of the second housing unit 40 and that portion of connection means 16 contained therein are shown in more detail in FIG. 5. As can be seen the portion of the connection means contained within the second housing unit is comprised of a wheel 81 with an opening 85 in the center to receive an axle. The second housing unit has an opening 89 into which wheel 81 is placed. The second housing unit also has a circular hole 83 on each side through which a bolt 84, which is threaded on the inside and screw 87 are placed, forming an axle upon which the connection means contained within the second housing unit can rotate. To assemble the device, wheel 81 is positioned in opening 89 of the second housing unit 40. Bolt 84 is then positioned through the holes 83 in the second housing unit and hole 82 in wheel 81. Bolt 84 is then secured by screw 88. Wheel 81 rotates about this axle thereby imparting a pivoting motion of up to 90 degrees in each direction. This pivoting motion accommodates the bending or the flexion-extension motion of the braced hip joint.

Figure 6:
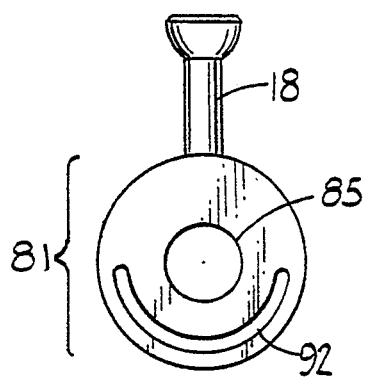
FIG. 6 is an elevational view of the connection means of this invention.
Figures 7, 7A:
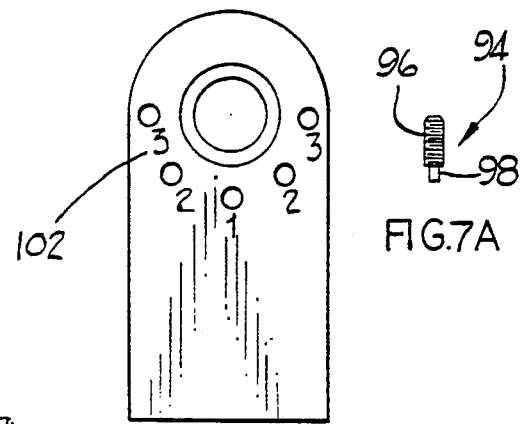
FIG. 7 is an elevational view of the side of the second housing unit which contains the stoppers.

With reference to FIG. 6, which shows the connection means in more detail, it can be seen that wheel 81 contains a groove 92 in one face. Referring to FIG. 7 it can be seen that the second housing unit contains stoppers 94 in the form of set screws which contain a threaded upper portion 96 and a smaller unthreaded lower portion 98. It can also be seen that one side of the second housing unit 40 contains a number of threaded screw holes 102. To control the degree of rotation, wheel 81 is positioned within the second housing unit such that the groove 92 is on the side of the unit which contains the screw holes as shown in FIG. 5. When assembled the unthreaded portion or pin 98 of screw 94 fits into the groove 92 on wheel 81. The wheel is allowed to rotate in either direction until the pin meets the end of the groove 92.

Figure 8A:
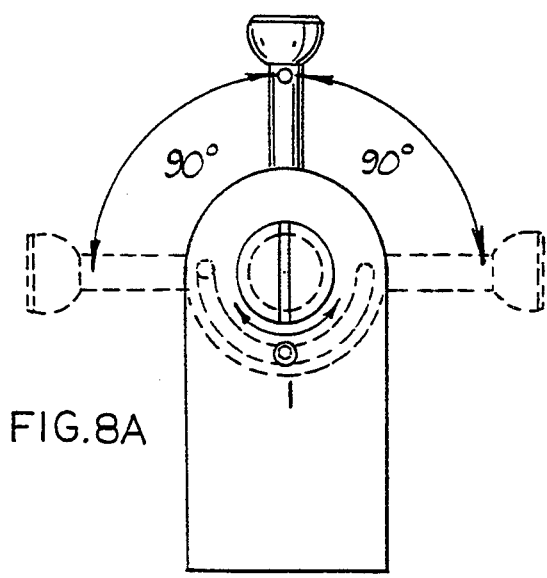
FIGS. 8A-8C are views showing the range of rotation of the second pivot mechanism which is contained within the second housing unit.
Figure 8B:
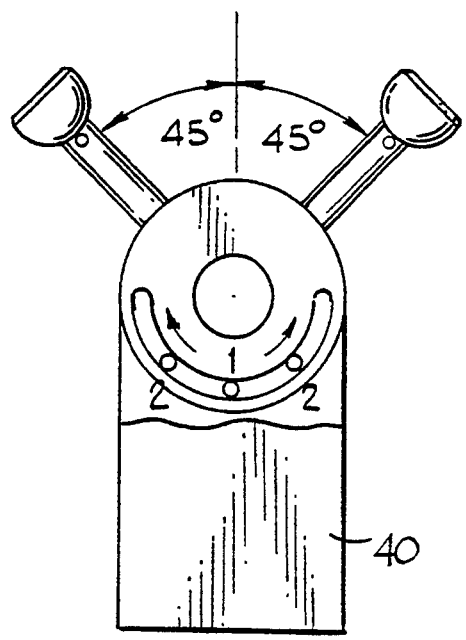
Figure 8C:
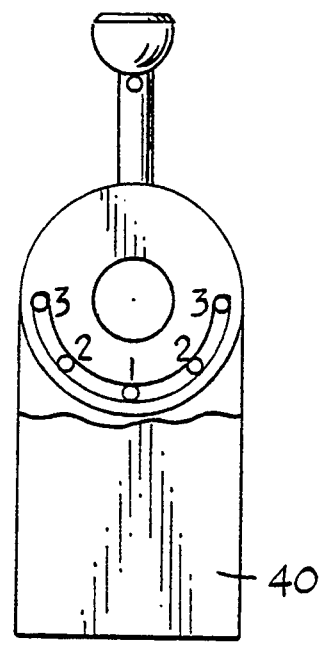

As shown in FIG. 8A when one screw is positioned in hole 1 the cylinder is permitted to rotate 90° in each direction. As shown in FIGS. 8B and 8C when the screws are placed in holes 2 the cylinder is permitted to rotate only 45° in each direction and when placed in holes 3 the cylinder cannot rotate at all, thereby preventing any flexion or extension of the leg.

In operation, it can be appreciated that design of this invention is such that the rotation means and pivoting means necessarily work in concert to approximate the ball-and-socket motion of the hip joint. Referring to FIG. 9 when the leg is extended the wheel 81 pivots about its axle to the extent permitted by the adjustment of the stop mechanism. As this happens the rotation means is able to rotate to the extent permitted by its stop mechanism to accommodate the outward rotation of the joint as the leg is extended.

What is claimed is:

1. An orthotic hip brace, comprising: a hip attachment means for attachment to a patient's hip; leg attachment means for attachment to a patient's leg; a first housing attached to one of the hip attachment means and leg attachment means; a second housing attached to the other of the hip attachment means and leg attachment means; a shaft connecting the first housing and second housing, the shaft having a knob at one end and a shaft wheel at the other end, the first housing having a sleeve to receive the shaft and a recess larger than the knob to receive the knob so that the shaft and knob can pivot laterally in the sleeve and recess to allow abduction and adduction of the patient's leg whereby the second housing can pivot in relation to the first housing to allow the patient's leg to be moved forward and backward, the second housing can rotate in relation to the first housing to allow the patient's leg to rotate, and the second housing can pivot laterally in relation to the first housing to allow the abduction and adduction of the patient's leg.

2. The brace of claim 1, wherein the shaft and knob are rotatable in the sleeve and recess to allow rotation of the patient's leg.

3. The brace of claim 2, wherein the second housing includes a slot and the shaft wheel is rotatably mounted in the slot.

4. The brace of claim 3, wherein the shaft wheel includes stop means and the second housing includes a pair of stops to abut against the shaft wheel stops to limit the degree of rotation of the shaft wheel in the second housing.

5. The brace of claim 4, wherein the stop means are the ends of an arcuate groove in the shaft wheel, and the second housing stops are pins in the second housing extending into said groove.

6. The brace of claim 5, wherein the pins are screws and the second housing includes a plurality of screw hole pairs to receive the screws to adjust the degree of allowed rotation of the shaft wheel in the second housing.

7. The brace of claim 3, wherein the shaft includes radially extending stop and the first housing includes stop means to abut against the shaft stop to limit the rotation of the shaft in the first housing.

8. The brace of claim 7, wherein the shaft stop includes a radially extending pin, and the stop means includes a pair of pins extending through the first housing, the depth to which the first housing pins extend through the housing being adjustable to adjust the degree of allowable shaft rotation.

9. The brace of claim 8, wherein the first housing pins are screws threadably mounted in the first housing.

* * * * *